US010577644B2

(12) United States Patent
Peter et al.

(10) Patent No.: US 10,577,644 B2
(45) Date of Patent: *Mar. 3, 2020

(54) METHOD FOR FRAGMENTING GENOMIC DNA USING CAS9

(71) Applicant: Agilent Technologies, Inc., Santa Clara, CA (US)

(72) Inventors: Brian Jon Peter, Los Altos, CA (US); Robert A. Ach, San Francisco, CA (US); Michael Walter, Blaubeuren (DE); Bram Herman, Letchworth Garden (GB)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 288 days.

This patent is subject to a terminal disclaimer.

(21) Appl. No.: 15/339,510

(22) Filed: Oct. 31, 2016

(65) Prior Publication Data
US 2017/0044592 A1 Feb. 16, 2017

Related U.S. Application Data

(63) Continuation of application No. 14/290,896, filed on May 29, 2014, now Pat. No. 9,873,907.

(60) Provisional application No. 61/828,507, filed on May 29, 2013, provisional application No. 61/831,061, filed on Jun. 4, 2013.

(51) Int. Cl.
C12Q 1/6806 (2018.01)
C12N 15/11 (2006.01)
C12Q 1/68 (2018.01)
C12P 19/34 (2006.01)
C12N 15/10 (2006.01)
C12Q 1/6869 (2018.01)
C12N 9/22 (2006.01)

(52) U.S. Cl.
CPC ............. C12Q 1/6806 (2013.01); C12N 9/22 (2013.01); C12N 15/1003 (2013.01); C12N 15/1034 (2013.01); C12Q 1/6869 (2013.01); C12Y 301/00 (2013.01); Y10T 436/143333 (2015.01)

(58) Field of Classification Search
None
See application file for complete search history.

(56) References Cited

U.S. PATENT DOCUMENTS

| 9,873,907 | B2 * | 1/2018 | Zeiner | ............ C12Q 1/6806 |
| 2010/0028873 | A1 | 2/2010 | Belauchi et al. | |
| 2014/0038241 | A1 | 2/2014 | Zhou et al. | |
| 2014/0127752 | A1 | 5/2014 | Zhou et al. | |

FOREIGN PATENT DOCUMENTS

| WO | 2013141680 A1 | 9/2013 |
| WO | 2013142578 A1 | 9/2013 |
| WO | 2013176772 A1 | 11/2013 |
| WO | 2013188638 A2 | 12/2013 |
| WO | 2014018423 A2 | 1/2014 |

OTHER PUBLICATIONS

Gasiunas, et al., "Cas9-crRNA ribonucleoprotein complex mediates specific DNA cleavage for adaptive immunity in bacteria", PNAS, Sep. 4, 2012, E2579-E2586.
Gnirke, et al., "Solution hybrid selection with ultra-long oligonucleotides for massively parallel targeted sequencing", Nature Biotechnology, vol. 27, No. 2, 2009, 182-189.
Jinek, et al., "A Programmable Dual-RNA-Guided DNA Endonuclease in Adaptive Bacterial Immunity", Science, vol. 337, Aug. 17, 2012, 37 Pages.
Jinek, et al., "RNA-programmed genome editing in human cells", eLife, 2013, 1-9.
Lecong, et al., "Multiplex Genome Engineering Using CRISPR/Cas Systems", Science, vol. 339, No. 6121, 2013, 819-823.
Mali, et al., "RNA-Guided Human Genome Engineering via Cas9", Science, vol. 339, No. 6121, 2013, 823-826.
Qi, et al., "Repurposing Crispr as an RNA-Guided Platform for Sequence-Specific Control of Gene Expression", Cell, vol. 152, No. 5, 2013, 1173-1183.
Kevinshe, "The big bad bac: bacterial artificial chromosomes", The Science Creative Quarterly, Aug. 2004.
Smolina, et al., "End invasion of peptide nucleic acids (PNAs) with mixed-base composition into linear DNA duplexes", Nucleic Acids Research, vol. 33, No. 17, 2005, 1-9.
Watanabe, et al., "Sequence Analysis of Amplified DNA Fragments Containing the Region Encoding the Putative Lipase Substrate-Binding Domain and Genotyping of Aeromonas hydrophila", Applied and Environmental Microbiology, Jan. 2004, 145-151.
Wu, et al., "Genome-wide binding of the CRISPR endonuclease Cas9 in mammalian cells", Nature Biotechnology, 2014, 1-9.
Advisory Action for U.S. Appl. No. 14/290,896, dated Aug. 17, 2017.
Notice of Allowance for U.S. Appl. No. 14/290,896, dated Sep. 14, 2017.

* cited by examiner

Primary Examiner — Channing S Mahatan

(57) ABSTRACT

A method for fragmenting a genome is provided. In certain embodiments, the method comprises: (a) combining a genomic sample containing genomic DNA with a plurality of Cas9-gRNA complexes, wherein the Cas9-gRNA complexes comprise a Cas9 protein and a set of at least 10 Cas9-associated guide RNAs that are complementary to different, pre-defined, sites in a genome, to produce a reaction mixture; and (b) incubating the reaction mixture to produce at least 5 fragments of the genomic DNA. Also provided is a composition comprising at least 100 Cas9-associated guide RNAs that are each complementary to a different, pre-defined, site in a genome. Kits for performing the method are also provided. In addition, other methods, compositions and kits for manipulating nucleic acids are also provided.

20 Claims, 1 Drawing Sheet

1. Start with randomly sheared long DNA fragments (>50kb)
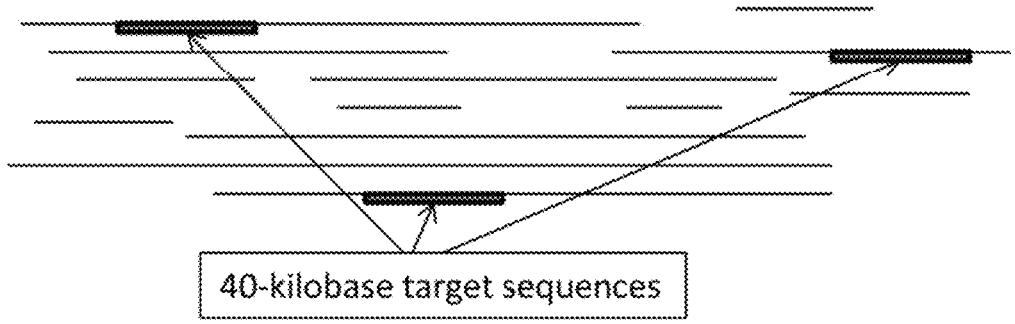
40-kilobase target sequences
2. Program Cas9 to bind and cleave sequence flanking 40kb targets
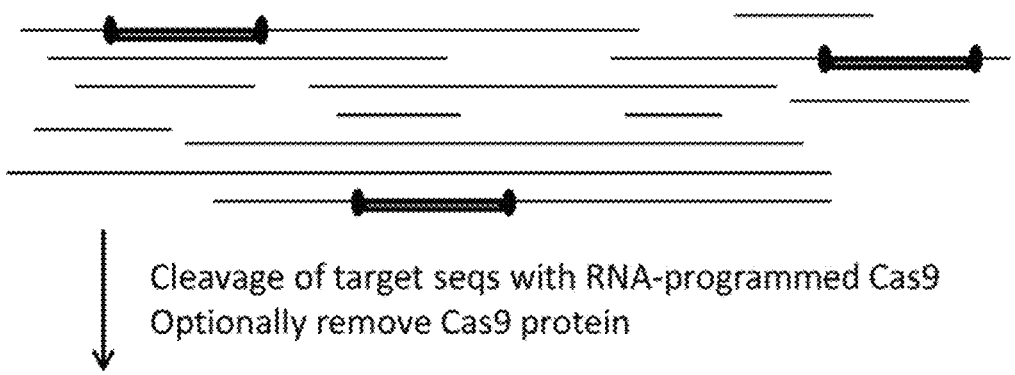
Cleavage of target seqs with RNA-programmed Cas9
Optionally remove Cas9 protein
3. Clone 40kb fragments into fosmid vectors (after optional size selection)
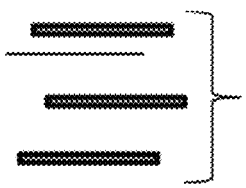
Clone into fosmid library; library will be enriched for 40 kb target seqs.

METHOD FOR FRAGMENTING GENOMIC DNA USING CAS9

CROSS-REFERENCING

This application is a continuation of U.S. application Ser. No. 14/290,896, filed May 29, 2014, which is incorporated by reference herein. This application also claims the benefit of U.S. provisional application Ser. No. 61/828,507, filed May 29, 2013 and 61/831,061 filed Jun. 4, 2013, which applications are incorporated by reference herein.

BACKGROUND

Methods for fragmenting a genome find use in a variety of genomic analysis applications, including, but not limited to SNP analysis, sequencing, mutation detection and the detection of chromosomal rearrangements.

SUMMARY

The present disclosure provides, inter alia, a method for fragmenting a genome. In certain embodiments, the method comprises: (a) combining a genomic sample containing genomic DNA with a plurality of Cas9-gRNA complexes, wherein the Cas9-gRNA complexes comprise a Cas9 protein and a set of at least 10 Cas9-associated guide RNAs that are complementary to different, pre-defined, sites in a genome, to produce a reaction mixture; and (b) incubating the reaction mixture to produce at least 5 fragments of the genomic DNA. Also provided is a composition comprising at least 100 Cas9-associated guide RNAs that are each complementary to a different, pre-defined, site in a genome. Kits for performing the method are also provided. Further provided are other methods, compositions and kits for manipulating nucleic acids.

BRIEF DESCRIPTION OF THE FIGURES

FIG. 1 schematically illustrates a method for fragmenting a genome.

DEFINITIONS

The term "sample" as used herein relates to a material or mixture of materials, typically, although not necessarily, in liquid form, containing one or more analytes of interest. A sample may have a complexity of least $10^3$, at least 10, at least $10^5$, $10^6$ or $10^7$ or more.

The term "nucleic acid sample," as used herein denotes a sample containing nucleic acids.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "target polynucleotide," as used herein, refers to a polynucleotide of interest under study. In certain embodiments, a target polynucleotide contains one or more sequences that are of interest and under study.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 10 to 50 nucleotides in length. Oligonucleotides may contain ribonucleotide monomers (i.e., may be oligoribonucleotides) or deoxyribonucleotide monomers. An oligonucleotide may be 10 to 20, 21 to 30, 31 to 40, 41 to 50, 51-60, 61 to 70, 71 to 80, 80 to 100, 100 to 150, 150 to 200, or 200 to 250 nucleotides in length, for example.

The terms "double stranded" and "duplex" as used herein, describes two complementary polynucleotides that are base-paired, i.e., hybridized together.

The term "amplifying" as used herein refers to generating one or more copies of a target nucleic acid, using the target nucleic acid as a template.

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "single nucleotide polymorphism," or "SNP" for short, refers to single nucleotide position in a genomic sequence for which two or more alternative alleles are present at appreciable frequency (e.g., at least 1%) in a population.

The term "free in solution," as used here, describes a molecule, such as a polynucleotide, that is not bound or tethered to another molecule.

The term "partitioning," with respect to a genome, refers to the separation of one part of the genome from the remainder of the genome to produce a product that is isolated from the remainder of the genome. The term "partitioning" encompasses enriching.

The term "genomic region," as used herein, refers to a region of a genome, e.g., an animal or plant genome such as the genome of a microbe (e.g., a bacterium), human, monkey, rat, fish or insect or plant. In certain cases, an oligonucleotide used in the method described herein may be designed using a reference genomic region, i.e., a genomic region of known nucleotide sequence, e.g., a chromosomal region whose sequence is deposited at NCBI's Genbank database or other databases, for example. Such an oligonucleotide may be employed in an assay that uses a sample containing a test genome, where the test genome contains a cleaving site for a nicking endonuclease adjacent to a binding site for the oligonucleotide. The precise nucleotide sequence that flanks the oligonucleotide binding site in a test genome may be known or unknown.

The term "affinity tag," as used herein, refers to moiety that can be used to separate a molecule to which the affinity tag is attached from other molecules that do not contain the affinity tag. In certain cases, an "affinity tag" may bind to the "capture agent," where the affinity tag specifically binds to the capture agent, thereby facilitating the separation of the molecule to which the affinity tag is attached from other molecules that do not contain the affinity tag. Examples of affinity tags include biotin, digoxygenin, peptide tags, and protein tags (e.g., his-tags and the like).

As used herein, the term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$M. A biotin affinity agent may also include a linker, e.g., -LC-biotin, -LC-Biotin, -SLC-Biotin or -PEG$_n$-Biotin where n is 3-12.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

The term "adaptor-ligated," as used herein, refers to a nucleic acid that has been ligated to an adaptor. The adaptor can be ligated to a 5' end and/or a 3' end of a nucleic acid molecule.

The term "adaptor" refers to a nucleic acid that is ligatable to one or both strands of a double-stranded DNA molecule. In some embodiments, an adaptor may be a hairpin adaptor. In another embodiment, an adaptor may itself be composed of two distinct oligonucleotide molecules that are base paired with one another. As would be apparent, a ligatable end of an adaptor may be designed to compatible with overhangs made by cleavage by a restriction enzyme, or it may have blunt ends.

The term "genotyping," as used herein, refers to any type of analysis of a nucleic acid sequence, and includes sequencing, polymorphism (SNP) analysis, and analysis to identify rearrangements.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche etc. Next-generation sequencing methods may also include nanopore sequencing methods or electronic-detection based methods such as Ion Torrent technology commercialized by Life Technologies.

The term "target sequence" refers to a sequence in a double-stranded DNA molecule, where the target sequence is bound, and, optionally cleaved or nicked by Cas9. In many cases, a target sequence may be unique in any one starting molecule and, as will be described in greater detail below, multiple different starting molecules (e.g., overlapping fragments) may contain the same target sequence. In some cases, the target sequence may be degenerate, that is, the target sequence may have base positions that may have variable bases. These positions may be denoted as Y, R, N, etc., where Y and R denote pyrimidine and purine bases, respectively, and N denotes any of the 4 bases.

The term "cleaving," as used herein, refers to a reaction that breaks the phosphodiester bonds between two adjacent nucleotides in both strands of a double-stranded DNA molecule, thereby resulting in a double-stranded break in the DNA molecule.

The term "nicking," as used herein, refers to a reaction that breaks the phosphodiester bond between two nucleotides in one strand of a double-stranded DNA molecule to produce a 3' hydroxyl group and a 5' phosphate group.

The terms "cleavage site," and "nick site," as used herein, refers to the site at which a double-stranded DNA molecule has been cleaved or nicked.

The term "Cas9-associated guide RNA" refers to a guide RNA as described above (comprising a crRNA molecule and a tracrRNA molecule, or comprising an RNA molecule that includes both crRNA and tracrRNA sequences). The Cas9-associated guide RNA may exist as isolated RNA, or as part of a Cas9-gRNA complex.

Reference to a Cas9-associated guide RNA is "complementary to" another sequence is not intended to mean that the entire guide RNA is complementary to the other sequence. A Cas9-associated guide RNA that is complementary to another sequence comprises a sequence that is complementary to the other sequence. Specifically, it is known that a Cas9 complex can specifically bind to a target sequence that has as few as 8 or 9 bases of complementarity with the guide Cas9-associated guide RNA in the complex. Off site binding can be decreased by increasing the length of complementarity, e.g., to 15 or 20 bases.

The terms "Cas9 enzyme" and "Cas9-gRNA complex" refer to a complex comprising a Cas9 protein and a guide RNA (gRNA). The guide RNA may be composed of two molecules, i.e., one RNA ("crRNA") which hybridizes to a target and provides sequence specificity, and one RNA, the "tracrRNA", which is capable of hybridizing to the crRNA. Alternatively, the guide RNA may be a single molecule (i.e., a sgRNA) that contains crRNA and tracrRNA sequences. A Cas9 protein may be at least 60% identical (e.g., at least 70%, at least 80%, or 90% identical, at least 95% identical or at least 98% identical or at least 99% identical) to a wild type Cas9 protein, e.g., to the *Streptococcus pyogenes* Cas9 protein. The Cas9 protein may have all the functions of a wild type Cas 9 protein, or only one or some of the functions, including binding activity, nuclease activity, and nuclease activity.

For Cas9 to successfully bind to DNA, the target sequence in the genomic DNA should be complementary to the gRNA sequence and must be immediately followed by the correct protospacer adjacent motif or "PAM" sequence. The PAM sequence is present in the DNA target sequence but not in the gRNA sequence. Any DNA sequence with the correct target sequence followed by the PAM sequence will be bound by Cas9. The PAM sequence varies by the species of the bacteria from which Cas9 was derived. The most widely used Type 11 CRISPR system is derived from *S. pyogenes* and the PAM sequence is NGG located on the immediate 3' end of the gRNA recognition sequence. The PAM sequences of Type 11 CRISPR systems from exemplary bacterial species include: *Streptococcus pyogenes* (NGG), *Neisseria meningitidis* (NNNNGATT), *Streptococcus thermophilus* (NNAGAA) and *Treponema denticola* (NAAAAC).

The term "Cas9 nickase" refers to a modified version of the Cas9-gRNA complex, as described above, containing a single inactive catalytic domain, i.e., either the RuvC- or the HNH-domain. With only one active nuclease domain, the Cas9 nickase cuts only one strand of the target DNA, creating a single-strand break or "nick". A Cas9 nickase is still able to bind DNA based on gRNA specificity, though nickases will only cut one of the DNA strands. The majority of CRISPR plasmids currently being used are derived from *S. pyrgenes* and the RuvC domain can be inactivated by an amino acid substitution at position D10 (e.g., DIOA) and the HNH domain can be inactivated by an by an amino acid substitution at position H840 (e.g., H840A), or at positions corresponding to those amino acids in other proteins. As is known, the D10 and H840 variants of Cas9 cleave a Cas9-induced bubble at specific sites on opposite strands of the DNA. Depending on which mutant is used, the guide RNA-hybridized strand or the non-hybridized strand may be cleaved.

The term "mutant Cas9 protein that has inactivated nuclease activity" refers to a Cas protein that has inactivated HNH and RuvC nucleases. Such a protein can bind to a target site in double-stranded DNA (where the target site is determined by the guide RNA), but the protein is unable to cleave or nick the double-stranded DNA.

As used herein and unless indicated to the contrary, the term "Cas9-fragment complex" refers to a complex containing a Cas9-gRNA and a DNA fragment to which the Cas9-gRNA complex binds.

DESCRIPTION OF EXEMPLARY EMBODIMENTS

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The following references are explicitly incorporated by reference for their teachings on Cas9, gRNA, and other reagents that can be used herein: Gasiunas et al (Proc. Natl. Acad. Sci. 2012 109: E2579-E2586), Karvelis et al (Biochem. Soc. Trans. 2013 41:1401-6), Pattanayak et al (Nat. Biotechnol. 2013 31: 839-43), Jinek et al. (Elife 2013 2: e00471), Jiang et al (Nat. Biotechnol. 2013 31:233-9), Hwang et al (Nat. Biotechnol. 2013 31: 227-9), Mali et al (Science 2013 339:823-6), Cong et al (Science. 2013 339: 819-23), DiCarlo et al (Nucleic Acids Res. 2013 41: 4336-43) and Qi et al (Cell. 2013 152: 1173-83).

As would be appreciated, the method described below may be employed to fragment a wide variety of different types of DNA, including plasmids, cDNA and genomic DNA.

Method for Fragmenting Genomic DNA

As noted above, a method for fragmenting a genome is provided. In certain embodiments, the method comprises: (a) combining a genomic sample containing genomic DNA with a plurality of Cas9-gRNA complexes, wherein the Cas9-gRNA complexes comprise a Cas9 protein and a set of at least 10 Cas9-associated guide RNAs that are complementary to different, pre-defined, sites in a genome, to produce a reaction mixture; and (b) incubating the reaction mixture to produce at least 5 fragments of the genomic DNA.

As would be apparent, this reaction may be done in vitro, i.e., in a cell-free environment using isolated genomic DNA. The method may be used to isolate double-stranded DNA fragments from virtually any source, including but not limited to total genomic DNA and complementary DNA (cDNA), plasmid DNA, mitochondrial DNA, synthetic DNA, and BAC clones, etc. Furthermore, any organism, organic material or nucleic acid-containing substance can be used as a source of nucleic acids to be processed in accordance with the present method including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, wherein certain embodiments the mammal is a human. In the description set forth above and below the method is used to fragment genomic DNA. However, it is recognized that the same method can be used to fragment DNA from other sources, e.g., cDNA.

The genomic DNA may be isolated from any organism. The organism may be a prokaryote or a eukaryote. In certain cases, the organism may be a plant, e.g., *Arabidopsis* or maize, or an animal, including reptiles, mammals, birds, fish, and amphibians. In some cases, the test genome may be human or rodent, such as a mouse or a rat. Methods of preparing genomic DNA for analysis is routine and known in the art, such as those described by Ausubel, F. M. et al., (*Short protocols in molecular biology*, 3rd ed., 1995, John Wiley & Sons, Inc., New York) and Sambrook, J. et al. (*Molecular cloning: A laboratory manual*, $2^{nd}$ ed., 1989, Cold Spring Harbor Laboratory Press, Cold Spring Harbor, N.Y.). In certain cases, the sample used may contain total genomic DNA, which may be unamplified or amplified, e.g., genomic DNA that has been amplified by a whole genome amplification method, that may or may not be already fragmented by other means, e.g., fragmented into fragments that are over 10 kb, or over 50 kb in length.

The guide RNAs used in the method may be designed so that they direct binding of the Cas9-gRNA complexes to pre-determined cleavage sites in a genome. In certain cases, the cleavage sites may be chosen so as to release a fragment that contains a region of unknown sequence, or a region containing a SNP, nucleotide insertion, nucleotide deletion, rearrangement, etc. Since genomic isolation methods, and the nucleotide sequences of many organisms (including many bacteria, fungi, plants and animals, e.g., mammals such as human, primates, and rodents such as mouse and rat) are known, designing guide RNAs for use in the present method should be within the skill of one of skilled in the art.

Cas9-gRNA complexes can be programmed to bind to any sequence, provided that the sequence has a PAM motif. In theory, the Cas9-gRNA complexes could cleave the genomic DNA to produce fragments in the range of 30-50 bp. However, in practice, the minimal interval between the cleavage sites may be e.g., in the range of 50-200 bp.

The Cas9-gRNA complexes may comprise a set of at least 10, at least 100, at least 1,000, at least 10,000, at least 50,000 or at least 100,000 or more different Cas9-associated guide RNAs that are each complementary to a different, pre-defined, site in a genome. The distance between neighboring sites may vary greatly depending on the desired application. In some embodiments, the distance between neighboring sites is in the range of 1 kb to 200 kb, and, in particular embodiments, the sites may be chosen to release fragments of a similar, defined, size, e.g., where at least 95% of the predicted fragments have a size that is within 20%, within 10% or within 5% of a chosen size, where the chosen size is in the range of 1 kb to 10 kb or 10 kb to 100 kb, for example. In certain cases, cleavage sites for the Cas9-gRNA complexes may be chosen to release fragments that are of a size suitable for cloning into a particular vector, e.g., a cosmid, fosmid, bac or bacteriophage, that only accepts fragments of a particular size.

In these embodiments, fosmid clones have been useful for genomic analysis due to their restricted length (~37 to 42 kb) and ability to preserve human sequence in *E. coli* without extensive rearrangement. However, a disadvantage of fosmid cloning approaches is the inability to target desired sequences. In this embodiment, one can design custom Cas9/CRISPR nucleases programmed with guide RNAs that target the enzyme to the ends of a set of approximately 40-kilobase fragments. After cleavage of the genome with the Cas9/CRISPR nucleases, the fraction of total DNA in the size range of 40 kb would be enriched for the target segments. This DNA could be cloned into fosmid vectors and the resulting library would be enriched for 40 kilobase target sequences, suitable for long-read sequencing. Careful preparation of genomic DNA with an average length above 50 kb (e.g., using specialized kits such as Qiagen's Genomic Tips or the MegaLong kit from G Biosciences) will improve the efficiency of recovering target fragments and will decrease the fraction of off-target sequences.

The method may be used to produce at least 10, at least 100, at least 1,000, at least 10,000, at least 50,000 or at least 100,000 or more fragments of a genome. Depending on how the method is implemented, the fragments may be distributed throughout the genome, or they may be distributed in one or more specific regions of a genome (e.g., 1, at least 10, at least 50, at least 100 or at least 1,000) or more specific regions), where each region may be cleaved to produce multiple fragments.

In some cases, the fragments produced by the method may be cloned into a vector, e.g., a fosmid, bac or cosmid vector for storage and later analysis. In some cases, the fragments may be treated with Taq polymerase to produce that contain a 3' A overhang, and then cloned by TA cloning, The fragments (whether or not they are cloned in a vector) may be genotyped, e.g., sequenced. In some cases, the fragments may be amplified prior to cloning and/or analysis, which may involve ligating adaptors onto the ends of the fragments, and amplifying the fragments using primers that hybridize to the ligated adaptors.

In particular embodiments, the fragments may be sequenced. In certain embodiments, the fragment may be amplified using primers that are compatible with use in, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure et al (Science 2005 309: 1728-32); Imelfort et at (Brief Bioinform. 2009 10:609-18); Fox et al (Methods Mol Biol. 2009; 553:79-108); Appleby et al (Methods Mol Biol. 2009; 513:19-39) and Morozova et al (Genomics. 2008 92:255-64), which are incorporated by reference for the general descriptions of the methods and the particular steps of the methods, including all starting products, reagents, and final products for each of the steps. In some cases, the fragments may be subjected to target enrichment methods prior to sequencing. Target enrichment methods are known in the art and encompass methods such as SureSelect and HaloPlex technologies commercialized by Agilent Technologies, PCR-amplification based strategies, and the like.

In one embodiment, the fragments may be sequenced using nanopore sequencing (e.g. as described in Soni et al. 2007 Clin Chem 53: 1996-2001, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology is disclosed in U.S. Pat. Nos. 5,795,782, 6,015,714, 6,627,067, 7,238,485 and 7,258,838 and U.S. Pat Appln Nos. 2006003171 and 20090029477.

Additionally, the reaction mixture may also comprise a set of Cas9-associated guide RNAs that are complementary to repetitive sequences in the genomic DNA, and the incubating results in cleavage of the repetitive sequences. This method may used to effectively remove repetitive sequence from a sample, where the term "repetitive sequence" refers to a segment of DNA containing a sequence of nucleotides that is repeated for at least 5, 10, 15, 20, 30, 40, 50, 60, 80, or 100 or more times. Repetitive sequences can include single nucleotide repeats (homopolymer stretches, e.g., poly A or poly T tails), di-nucleotide repeats (e.g., ATAT or AGAG), tri-nucleotide repeats, tetranucleotide repeats, telomeric repetitive elements and the like. Repetitive sequences also include, but not limited to, ALU, LINE (long interspersed genetic elements, which are non-coding), SINE (short interspersed genetic elements, which also are non-coding), and certain transposons such as L and P element sequences. ALU elements are a type of SINE element, roughly 300 base pairs in length. In certain embodiments, the repeat sequences may be cleaved to any suitable size, e.g., to a size in the range of 13-200 bases and each repeat may be cleaved at multiple sites. In some cases, the repetitive sequences are cleaved into fragments that range in size from 20 bases to 1 kb. The smaller fragments (the repetitive sequences) may be separated from the larger fragments (containing the non-repetitive sequences) by any suitable method, including by size exclusion. The longer fragments can be processed (e.g., cloned, amplified, sequenced, etc.). In some embodiments, certain longer fragments may be selected by target enrichment prior to further analysis. Such methods are known in the art, for example, methods described in U.S. Pat. No. 8,017,328 and US patent application US20130323725, which are incorporated herein by reference.

In certain embodiments, inhibitors of DNases can be used to reduce degradation of DNA. DNase inhibitors that are compatible with Cas9 include, but are not limited to, 2-mercaptoethanol and actin.

In some embodiments, the method may further comprise analyzing the genome after cleavage of one or more repetitive sequences.

In some embodiments, the method may comprise enriching a fraction of the genome after cleavage of one or more repetitive sequences.

Compositions

In addition to the method described above, a number of compositions are also provided. In certain embodiments, the composition may contain a set of at least 10 Cas9-associated guide RNAs that are each complementary to a different, pre-defined, site in a genome. The composition may comprise, e.g., at least 10, at least 15, at least 20, at least 30, at least 50, at least 75, at least 100, at least 200, at least 300, at least 400, at least 500, at least 600, at least 700, at least 800, at least 900, at least 1,000, or at least 10,000 or more guide RNAs. The sites to which the Cas9-associated guide RNAs bind are immediately downstream from a PAM trinucleotide (e.g., CCN). The guide RNAs may be in solution, or they may be in dried form, e.g., lyophilized. The guide RNAs may be at least 20, at least 30, at least 50, at least 75, at least 100, at least 150, at least 180, at least 200, at least 220, at least 240, or at least 260 nucleotides long. Such compositions may be employed in any embodiment disclosed herein.

As would be apparent, the composition may additionally contain a single Cas9 protein. The composition may also contain genomic DNA, e.g., microbial or mammalian genomic DNA such as human genomic DNA.

The guide RNAs may be synthesized on a solid support in an array, where the oligonucleotides are grown in situ. Oligonucleotide arrays can be fabricated using any means, including drop deposition from pulse jets or from fluid-filled tips, etc., or using photolithographic means. Polynucleotide precursor units (such as nucleotide monomers), in the case of in situ fabrication can be deposited. Oligonucleotides synthesized on a solid support may then be cleaved off to generate the population of oligonucleotides. Such methods are described in detail in, for example U.S. Pat. Nos. 7,385,050, 6,222,030, 6,323,043, and US Pat Appln Pub No. 200210058802, etc., the disclosures of which are incorporated herein by reference. The oligonucleotides may be tethered to a solid support via a cleavable linker, and cleaved from the support before use.

In some embodiments, the Cas9-associated guide RNAs are each specific for a different, pre-defined, site in genomic DNA.

In some embodiments, the Cas9-associated guide RNAs are each specific for a different, pre-defined, site in mammalian genomic DNA.

In some embodiments, the Cas9-associated guide RNAs that are each specific for a different, pre-defined, site in human genomic DNA.

In some embodiments, the Cas9-associated guide RNAs are each specific for a different, pre-defined, site in microbial genomic DNA.

In some embodiments, the composition comprises one or a plurality of Cas9-associated guide RNA binding to the genome of one pathogen and one or a plurality of Cas9-associated guide RNA binding to the genome of another pathogen.

In some embodiments, the sites to which the Cas9-associated guide RNAs bind are spaced along the genomic DNA at a defined interval.

In some embodiments, the defined interval is in the range of 1 kb to 100 kb.

In some embodiments, the composition further comprises a set of Cas9-associated guide RNAs that are capable of binding repetitive sequences in genomic DNA.

In some embodiments, the composition further comprises a Cas9 nuclease.

In some embodiments, the Cas9-associated guide RNAs are in solution as a mixture.

In some embodiments, the Cas9-associated guide RNAs are tethered to a substrate in an array. In some embodiments, the composition comprises a DNase inhibitor.

Kits

Also provided by the subject invention are kits for practicing the subject method, as described above. The subject kit contains mutant Cas9 protein and set of at least 2, at least 5, at least 10, at least 15, at least 20, at least 30, at least 50, at least 75, at least 100, at least 200, at least 300, at least 400, at least 500, at least 600, at least 700, at least 800, at least 900, at least 1,000, or at least 10,000 or more guide RNAs, as described above. The guide RNAs may in the form of a dried pellet or an aqueous solution. The guide RNAs may be at least 20, at least 30, at least 50, at least 75, at least 100, at least 150, at least 180, at least 200, at least 220, at least 240, or at least 260 nucleotides long.

In addition to the instructions, the kits may also include one or more control genomes and or oligonucleotides for use in testing the kit. The subject kit may further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kit as a package insert, in the labeling of the container of the kit or components thereof (i.e., associated with the packaging or subpackaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

The various components of the kit may be in separate containers, where the containers may be contained within a single housing, e.g., a box.

In some embodiments, the Cas9-associated guide RNAs are each specific for a different, pre-defined, site in genomic DNA.

In some embodiments, the Cas9-associated guide RNAs are each specific for a different, pre-defined, site in mammalian genomic DNA.

In some embodiments, the Cas9-associated guide RNAs that are each specific for a different, pre-defined, site in human genomic DNA.

In some embodiments, the Cas9-associated guide RNAs are each specific for a different, pre-defined, site in microbial genomic DNA.

In some embodiments, the kit comprises one or a plurality of Cas9-associated guide RNA binding to the genome of one pathogen and one or a plurality of Cas9-associated guide RNA binding to the genome of another pathogen.

In some embodiments, the sites to which the Cas9-associated guide RNAs bind are spaced along the genomic DNA at a defined interval.

In some embodiments, the defined interval is in the range of 1 kb to 100 kb.

In some embodiments, the kit further comprises a set of Cas9-associated guide RNAs that are capable of binding repetitive sequences in genomic DNA.

In some embodiments, the kit further comprises a Cas9 nuclease.

In some embodiments, the Cas9-associated guide RNAs are in solution as a mixture.

In some embodiments, the Cas9-associated guide RNAs are tethered to a substrate in an array. In some embodiments, the kit comprises a DNase inhibitor.

Utility

The above-described method may be used to fragment a genome in a defined way, i.e., to produce fragments of one or more chosen regions of a genome. The fragments produced by the subject method may be arbitrarily chosen or, in some embodiments, may have a common function, structure or expression. While the above-described method is not so limited, the method may be employed to isolate promoters, terminators, exons, introns, entire genes, homologous genes, sets of gene sequences that are linked by function, expression or sequence, regions containing insertion, deletion or translocation breakpoints or SNP-containing regions, for example. Alternatively, the method could be used to reduce the sequence complexity of a genome prior to analysis, or to enrich for genomic regions of interest.

In certain embodiments the method may be used to produce fragments of interest (i.e., one or more regions of a genome), where the resultant sample is at least 50% free, e.g., at least 80% free, at least 90% free, at least 95% free, at least 99% free of the other parts of the genome. In particular embodiments, the products of the method may be amplified before analysis. In other embodiments, the products of the method may be analyzed in an unmodified form, i.e., without amplification.

As noted above, the method may be employed to isolate a region of interest from a genome. The isolated region may be analyzed by any analysis method including, but not limited to, DNA sequencing (using Sanger, pyrosequencing or the sequencing systems of Roche/454, Helicos, Illumina/Solexa, and ABI (SOLiD)), a polymerase chain reaction assay, a hybridization assay, a hybridization assay employing a probe complementary to a mutation, a microarray assay, a bead array assay, a primer extension assay, an enzyme mismatch cleavage assay, a branched hybridization assay, a NASBA assay, a molecular beacon assay, a cycling probe assay, a ligase chain reaction assay, an invasive cleavage structure assay, an ARMS assay, or a sandwich hybridization assay, for example. Some products (e.g., single-stranded products) produced by the method may be sequenced, and analyzed for the presence of SNPs or other differences relative to a reference sequence. As would be clear to one skilled in the art, the proposed method may be useful in several fields of genetic analysis, by allowing the artisan to focus his or her analysis on a genomic region of interest.

The subject method finds particular use in SNP haplotyping of a chromosomal region that contains two or more SNPs, for enriching for DNA sequences for paired-end sequencing methods, for generating target fragments for long-read sequences, isolating inversion, deletion, and translocation breakpoints, for sequencing entire gene regions (exons and introns) to uncover mutations causing aberrant splicing or regulation, and for the production of long probes for chromosome imaging, e.g., Bionanomatrix, optical mapping, or fiber-FISH-based methods.

In particular cases, the method described above can also be used for long-range haplotyping by using hemizygous deletions to differentially label maternal and paternal chromosomes. The method may be employed to capture such hemizygous sequences together with adjoining sequence. In this way, maternal and paternal copies of DNA could be separated and analyzed independently. This would enable haplotype phased sequencing.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

ALTERNATIVE EMBODIMENTS

Cas9-Transposase Fusion Proteins

A fusion protein comprising a Cas9 protein and a transposase is provided.

In some embodiments, the Cas9 protein has inactivated nuclease activity

In some embodiments, the Cas9 protein is fused to the N-terminus of the transposase.

In some embodiments, the Cas9 protein is fused to the C-terminus of the transposase.

A complex comprising a fusion protein comprising a Cas9 protein and a transposase is provided, where the complex further comprises a Cas9-associated guide RNA and a transposon.

In some embodiments, Cas9 protein and Cas9-associated guide RNA directs the transposon to a defined site in a genome, thereby allowing the transposase to insert the transposable element at a defined site.

In some embodiments, the transposon comprises one or more of a primer binding site, a molecular barcode or a promoter.

In some embodiments, the promoter is a Φ29 promoter.

Also provided is a method comprising contacting the complex with a genome, thereby causing the transposable element to be inserted into the genome proximal at a site to which the Cas9 protein binds.

In some embodiments, the method may be done by contacting a plurality of complexes with a genome, wherein each complex comprises a different guide RNA, and the different guide RNAs are complementary to defined sites in the genome, and inserting a plurality of transposons into the genome.

In some embodiments, the sites to which the guide RNAs bind are distributed across a target sequence at defined intervals (e.g., in the range of 100 bp to 5 kb), thereby producing transposon insertions at defined intervals.

In some embodiments, the sequences between the transposon insertions are amplified using PCR primers that bind to primer binding sites in the transposon insertions.

In some embodiments, the transposon is biotinylated.

In some embodiments, the transposase is a Sleeping Beauty, Piggybac or Tn5 transposase.

Transposases are enzymes derived from transposable elements that randomly break DNA and insert a transposable-element DNA that encodes the transposase. Transposases have been used in genetic and molecular biology applications to rapidly integrate DNA "tags" into a target sample of DNA (usually genomic DNA) as part of an insertional mutagenesis screen (in vivo) or more recently to create next-generation sequencing libraries (in vitro).

As with transposable element integration, the integration of DNA tags show little sequence bias except insertion between TA dinucleotides (which are duplicated during transposition and flank the integration site). For some next generation sequencing (NGS) applications applications, whole-genome surveys are benefitted by the random integration events garnered from transposition, which is the basis of the Nextera whole-genome library preparation technology from Illumina. However, for creating targeted NGS libraries, it would be advantageous to target a transposase to specific genomic locations to enable the rapid production of "directed" NGS libraries. The types of "targeted" NGS libraries envisioned here would obviate the hybridization-based selection approaches used in target capture protocols, as these selections take extra time, and could permit time-sensitive applications (such as diagnostics).

In this embodiment, Cas9/crRNA is used to provide an efficient targeting system to place desired sequences (e.g., barcodes, promoters, primer binding sites, etc.) in specific locations on target DNAs. In some embodiments, mutant Cas9 protein that has inactivated nuclease activity may targeted to a specific genomic locus for the purposes of: (a) rapidly producing a targeted next generation sequencing (NGS) library preparation suitable for diagnostic or research purposes via Cas9-targeted transposition of NGS adaptors or (b) Cas9-targeted transposition of a promoter, e.g., a minimal Φ29 origin of replication that will enable the isothermal amplification of >50 kb of "tagged" genomic DNAs, which can be used for amplification, isolation and detection of chromosomal rearrangements from tumor samples or the interrogation of unknown regions of microbial DNAs. The mutant Cas9 protein is inactivated in the sense that it can bind, but it cannot cleave, the sequence to which it has been programmed to bind by the gRNA complexed to it. In certain embodiments, the Cas9 protein has amino acid substitutions at D10 and H840, or sites corresponding thereto. In particular embodiments, the Cas9 protein may have D10A and H840A substitutions (or equivalent substitutions at positions corresponding to D10 and H840 in the Streptococcus Cas9 protein).

In one embodiment, a cas9$^{\Delta HNH/\Delta RuvC}$ transposase (such as ISY 100) fusion protein loaded with a transposon containing, e.g., next-generation sequencing (NGS) adaptors or common sequences that could be primed to generate NGS libraries by PCR, are produced. In this example, targeting the cas9-transposase fusion protein to specific gDNA loci will enable the targeted one-step integration of NGS adaptors at specific genomic sites, thus an NGS library that is ready for sequencing can be produced rapidly and without hybrid-selection approaches. An added feature could be the use of biotinylated DNA "tags" such that these targeted integrants may be separated from the gDNA that is not part of the NGS library.

A related approach could involve tethering wildtype (cleavage-competent) Cas9 to a topoisomerase linked to an NGS adaptor or other nucleic acid sequence. After dsDNA target cleavage, the topoisomerase can ligate the tethered NGS adaptor to the blunt ends generated by Cas9 cleavage and produce a similar outcome as (a) above.

Alternatively, the NGS adaptor in the method described above can be replaced with a minimal origin of replication for B. subtilis phage O29. This will result in the deposition of a O29 replication origin at a Cas9-directed genomic site. These replication origins, when containing a free 5'-phosphorylated end and a complex of four Φ29 proteins, will catalyze the isothermal replication of 50-100 kb of single-stranded DNA from the site of origin, owing to the high processivity of Φ29 DNA polymerase (P2). This replicated ssDNA contains a 5'-P-linked Φ29 terminal protein (P3) that can be used as a handle to isolate the replicated ssDNA from the rest of the sample. Once isolated, conventional NGS library or CGH array approaches can be used to interrogate the replicated ssDNA. This approach will be particularly useful for determining what sequences lie a significant distance downstream of a known sequence. For example, a small portion of a bacterial genome present in a complex metagenomic sample may be known, but more sequence of this bacterium is desired. Alternatively, a suspected chromosomal rearrangement may lie downstream of a particular locus, and the exact sequence surrounding the rearrangement may be desired.

In more detail, the origins of replication for Φ29 are 191 bp and 194 bp sequences derived from the left and right ends of the Φ29 genome, respectively. Smaller functional regions of these Φ29 replication origins have been partially mapped, and the smallest known functional Φ29 replication origin is 68 nt. These sequences bind to a complex of four Φ29 proteins—the Φ29 DNA polymerase and 'terminal protein mentioned above, P5 (a single-stranded DNA binding protein) and P6 (a double-stranded DNA binding protein).

The Φ29 replication complex involves coating and unwinding the Φ29 replication origin by the concerted actions of P5 and P6, and covalent attachment of P3 to the 5' end of the DNA, which serves to prime replication by P2 polymerase. No oligonucleotides are necessary to prime Φ29 transcription due to the presence of P3, thus Φ29 polymerase can extend multiple Φ29 replication origin integrants in parallel using the same four factors.

To generate a suitable set of ends for the integrated origin of replication, a unique cut site may be engineered into the Φ29 replication origin. One solution may be to incorporate a deoxyuracil in place of a thymidine at an appropriate location in the Φ29 origin. Addition of uracil deglycosylase (USER) will remove the uracil, and the second strand can be cleaved by addition of T7 endonuclease I. This will provide a terminus for Φ29 polymerase entry in conjunction with the other accessory factors.

This cas9::transposase-029 ORI approach could be applied to a slightly different application by adding two Φ29 ORIs to FFPE slides with reversed formaldehyde crosslinks. This system could be applied for the isothermal amplification and visualization (fluorescent or otherwise-detectable nucleotides) of large chromosomal amplicons, which may be detectable in situ by microscopic evaluation, or could otherwise provide a minimally destructive method for interrogating precious clinical samples by NGS.

Depending on how the method is implemented and how the products are sequenced, the new sequence insertions may be distributed along the product molecule with an average spacing that is in the range of 50 bases to 20 kb, e.g., 100 bases to 10 kb or 200 bases to 2 kb, for example. In other embodiments, the new sequence insertions may be distributed along the product molecule with an average spacing of 10 kb to 100 kb, for example.

The Cas9-protein may be fused to Sleeping Beauty, Piggybac or Tn5 transposons, among others. The disclosure of US20120208724 is incorporated by reference herein for all purposes.

Method for Overcoming a Transformation Barrier in a Bacterial Host

A method for overcoming a transformation barrier in a bacterial host is provided. In these embodiments, the method may comprise:

(a) identifying a bacterial host that is recalcitrant to transformation with a particular plasmid:

(b) knocking out the Cas9/CRISPR system in the bacterial host, (c) transforming the host with the knocked out Cas9/CRISPR system with the plasmid.

In certain embodiments, the Cas9/CRISPR system is knocked out by making a mutation in a Cas9 coding sequence in the genome of the host.

In certain embodiments, the Cas9/CRISPR system may be knocked out by expressing an anti-Cas9 protein into the host In certain embodiments, the host is an extremophile.

In certain embodiments, the host is an acidophile, an alkaliphile, an anaerobe, a cryptoendolith, a halophile, a hyperthermophile, a hypolith, a lithoautotroph, a metallotolerant, an oligotroph, an osmophile, a piezophile, a psychrophile, a radioresistant organism, a thermophile, a thermoacidophile or a xerophile.

In certain embodiments, the plasmid comprises an origin of replication and an antibiotic resistance gene.

Bioinformatic analyses suggest CRISPR-based innate immunity systems exist in >50% of all bacterial species and >90% of archaebacteria. In some species CRISPR represents a barrier to transformation, and that by eliminating CRISPR-based innate immunity we can make some microbial species amenable to genetic manipulation. A recent report described various anti-CRISPR proteins derived from phage (Bondy-Denomy et al, 2013 Nature 493:429-432). We propose that expression or co-transformation of anti-CRISPR protein or DNA can be used to overcome the transformation barrier in certain hosts. Using anti-CRISPR proteins to overcome barriers to transformation has a number of advantages: First, the presence of a CRISPR system in the host organism can be easily determined by genomic DNA sequence analysis. Second, co-expression of anti-CRISPR requires no a priori manipulation of the host genome. Third, inducible expression of anti-CRISPR proteins allows for negative selection of plasmids (ie plasmids are destroyed in a CRISPR-dependent fashion when anti-CRISPR protein expression is shut off).

In one embodiment, a plasmid encoding one or more anti-CRISPR proteins along with an antibiotic resistance gene and gene(s) of interest are transformed into a new host and transformants are selected based on antibiotic resistance. The presence of antibiotic resistant clones and the loss of antibiotic resistance when anti-CRISPR gene expression is turned off are phenotypes that indicate the barrier to transformation has been effectively eliminated. In a second embodiment, anti-CRISPR protein is co-transformed with said plasmid in order to ensure the plasmid is not restricted by an active CRISPR system before gene expression is established.

The method described above employed to make any bacterium competent for transformation with, e.g., a nucleic acid such as a vector that has an appropriate origin of replication. See, e.g., Johnsborg et al. Res. Microbiol 2007 158: 767-78, which is incorporated by reference. In some embodiments, the method finds particular use in transforming extremophilic bacteria or archaebacteria such as an acidophile (an organism with optimal growth at pH levels of 3 or below), an alkaliphile (an organism with optimal growth at pH levels of 9 or above), an anaerobe (an organism that does not require oxygen for growth such as *Spinoloricus Cinzia*) a cryptoendolith (an organism that lives in microscopic spaces within rocks), a halophile (an organism requiring at least 0.2M concentrations of salt (NaCl) for growth), hyperthermophile (an organism that can thrive at temperatures between 80-122° C.), a hypolith (an organism that lives underneath rocks in cold deserts), a lithoautotroph (an organism whose sole source of carbon is carbon dioxide and exergonic inorganic oxidation), a metallotolerant (which is capable of tolerating high levels of dissolved heavy metals in solution), an oligotroph (an organism capable of growth in nutritionally limited environments), an osmophile (an organism capable of growth in environments with a high sugar concentration), a piezophile (an organism that lives optimally at high pressures such as those deep in the ocean or underground), a psychrophile (an organism capable of survival, growth or reproduction at temperatures of −15° C. or lower for extended periods), a radioresistant organism that is resistant to high levels of ionizing radiation, a thermophile (an organism that can thrive at temperatures between 45-122° C.), a thermoacidophile (a combination of thermophile and acidophile that prefer temperatures of 70-80° C. and pH between 2 and 3) and a xerophile (which grows in extremely dry, desiccating conditions).

Method for SNP Detection

Also provided herein is a method for SNP detection.

In some embodiments, this method comprises:

(a) contacting a genomic sample that comprises a polymorphic site with a Cas9-gRNA complex that comprises an allele-specific guide RNA; and (b) determining whether the Cas9-gRNA complex cleaves the polymorphic site, wherein cleavage of the polymorphic site indicates the allele of the SNP at the polymorphic site.

In some embodiments, the genomic sample comprises mammalian genomic DNA.

In some embodiments, the genomic sample comprises human genomic DNA.

In some embodiments, the genomic sample comprises plant genomic DNA.

In some embodiments, the SNP is associated with a disease.

In some embodiments, the method comprises contacting the genomic sample with a plurality of Cas9-guide RNA complexes, wherein each guide RNA targets a particular SNP allele.

In some embodiments, the method comprises contacting the genomic sample with at least 1,000 Cas9-guide RNA complexes, each targeting a different SNP.

In some embodiments, the method cleavage products are analyzed by gel electrophoresis, mass spectrometry or by sequencing.

In this method, the term "single nucleotide polymorphism," or "SNP" or "SNP site" for short, refers to the single nucleotide position in a genomic sequence for which two or more alternative alleles are present at appreciable frequency (e.g., at least 1%) in a population. An "SNP allele" refers to the identity of the nucleotide of SNP. A "first allele" and a "second allele" of a SNP are different alleles, i.e., they have different SNP nucleotides. When a Cas9-gRNA complex cleaves near a SNP "only if a first allele is present," the Cas9-gRNA complex cleaves at a first allele of the SNP and not at a different (i.e., second) allele of the SNP.

Since the nucleotide sequences of hundreds of thousands of SNPs from humans, other mammals (e.g., mice), and a variety of different plants (e.g., corn, rice and soybean), are known (see, e.g., Riva et al 2004, *A SNP-centric database for the investigation of the human genome BMC Bioinformatics* 5:33; McCarthy et al. 2000 The use of single-nucleotide polymorphism maps in pharmacogenomics Nat Biotechnology 18:505-8) and are available in public databases (e.g., NCBI's online site-specific nicking endonuclease dbSNP database, and the online database of the International HapMap Project, see also Teufel et al. 2006 Current bioinformatics tools in genomic biomedical research *Int. J. Mol. Med.* 17:967-73), and several SNPs lie proximal to a PAM motif, designing guide RNAs that recognize and cleave at particular alleles of a SNP would be well within the skill of one skilled in the art.

Disease-associated allele variants can sometimes be identified as SNPs that change the restriction pattern of said sequence when digested with a given restriction enzyme and can be detected by a technique called Restriction Fragment Length Polymorphism (RFLP) mapping. Other allele variants of the same gene may generate SNPs cleavable by the same restriction enzyme, or a different restriction enzyme, or with no available enzymes. Consequently, there is no way to do a single RFLP digest to perform comprehensive SNP analysis of all known disease-associated allele variants. SNP analysis is also commonly used to classify species from environmental samples.

SNP analysis could be performed using Cas9 programmed with a library of guide RNAs that can uniquely identify known SNPs. Use of Cas9 allows for universal reaction conditions and ease of automation. Additionally, because Cas9 likely uses a scanning method for homology search, overlapping guide mRNAs should not interfere extensively with each other as they would with standard hybridization methods.

For a given SNP, a guide mRNA can be designed such that the unique sequence represented by the SNP is incorporated into the guide. Such a guide mRNA should program a Cas9 complex to cleave the SNP sequence but not the reference sequence. Digestions targeting multiple SNPs could be done in parallel (multiplexed) so that the presence/absence of a panel of SNP variants could be determined in a single reaction. Analysis of digestion products could be performed by gel electrophoresis, mass spectrometry, or other methods.

In certain embodiments, the method may be done using a panel of guide RNAs, where each guide RNA targets a particular SNP allele. The method may be used to analyze at least 2, at least 10, at least 1,000, at least 10,000 or at least 100,000 or more different SNPs in a sample, in parallel. The resultant fragments can be analyzed using any suitable method, including gel electrophoresis, mass spectrometry or sequencing.

Method for Detecting a Microbe

Also provided herein is a method for detecting a microbe in a sample.

Some embodiments of the method comprise:

(a) contacting a sample comprising microbial DNA with a Cas9-gRNA complex and a microbe-specific guide RNA; and (b) determining whether the Cas9-gRNA complex cleaves the microbial DNA, wherein cleavage of the microbial DNA indicates the microbe is in the sample.

In some embodiments, the microbial DNA is of unknown species.

In some embodiments, the microbe-specific guide RNA specifically hybridizes to a microbe that is associated with a disease.

In some embodiments, the method comprises contacting the sample with a plurality of Cas9-microbe-specific guide RNA complexes, wherein each guide RNA targets a different microbe.

In some embodiments, the method comprises contacting the sample with at least 1,000 Cas9-microbe-specific guide RNA complexes, each targeting a different microbe.

In some embodiments, the method cleavage products are analyzed by gel electrophoresis, mass spectrometry or by sequencing.

In this embodiment, the term "microbe," as used herein, refers to a microorganism. The term includes bacteria, fungi, archaea, and protists. The term "microbe" includes pathogenic bacteria, causing diseases such as plague, tuberculosis and anthrax; protozoa, causing diseases such as malaria, sleeping sickness and toxoplasmosis; and also fungi causing diseases such as ringworm, candidiasis or histoplasmosis, for example.

The guide RNAs used are microbe-specific in that they are capable of distinguishing between different microbes, where the term "different microbes" refers to microbes that are distinct from each other because they belong to a different genus, or to a different species or to a different strain. Two microbes that belong to different genera are considered to be different, microbes that belong to the same genus but to different strains are considered to be different, microbes that belong to the same genus and species but to different strains are also considered to be different.

S Many pathogens can cause food-borne illness and can be identified by specific PCR-based assays that identify unique DNA sequences in said pathogens' genome (see for example, Naravaneni and Jamil, *J Med. Microbiol.* 2005). In general, pathogens represent an extremely small fraction of the total sample but can still be dangerous at these low levels. Most technologies aiming to identify pathogens based on genomic sequences have difficulty in both precision and sensitivity. Additionally, rapid evolution of pathogens leads to rapid obsolescence of detection assays. Cas9 can be programmed with a library of guide mRNAs that can uniquely identify a large number of pathogens can provide a single, rapid assay for identification of said pathogens.

Cas9/crRNA can be used as an efficient targeting system to place desired protein and nucleic acid payloads (fused to Cas9) in specific locations on target DNAs. Here we use Cas9/crRNA as a tool to modify and subsequently identify rare DNA sequences in complex mixtures.

A Cas9-based assay addresses the precision problem by allowing one to design a large number of target sites in any pathogen genome to generate fragments for sequence analysis. There is no limitation for selecting unique sequences with an appropriate melting temperature that has proved difficult for any hybridization-based technologies. Likewise, because each target fragment must contain the precise ~24 base pair Cas9 recognition sequence at each end of the target, the potential for off-target cleavage and generation of fragments amenable to sequencing is rare. Sensitivity in a Cas9-based assay should be far superior to raw sequencing, since the vast majority of DNA in a sample will not be amenable for sequencing and because amplification of the small fraction of Cas9-generated fragments prior to sequencing is available.

In one embodiment, DNA is extracted from a food sample or culture and sheared into small fragments and treated with a chemical reagent that specifically reacts with 3' OH groups at the DNA ends and inhibits ligation (for example, 4-nitro isatoic anhydride, as described in Invention disclosure #20130128). Sheared fragments are then digested with a pool of Cas9 programmed with a guide mRNA library specific to from one to 100 unique pathogens. For each pathogen, pairs of sequences have been selected so that each pair is unique to a single pathogen of interest or to a family of pathogens, and is separated by 40 to 250 nucleotides. For each pathogen or pathogen family, from one to 1000 target pairs may be selected. Digested fragments are ligated at high efficiency to common PCR/sequencing primers, whereas DNA fragments with derivatized ends are not. The sample is then subject to PCR using said common primers to generate a binary output (PCR positive=pathogen positive) or subjected to sequencing for precise identification of one or more pathogen species.

In certain embodiments, the method may be done using a panel of guide RNAs, where each guide RNA targets a particular microbe. The method may be used to analyze at least 2, at least 10, at least 1,000, at least 10,000 or at least 1 (00,000 or more different microbes in a sample, in parallel. The resultant fragments can be analyzed using any suitable method, including gel electrophoresis, mass spectrometry or sequencing.

Guide RNAs used in this subject method may be designed by utilizing the genome sequence information as well as expressed gene sequence information available at several public and private databases, for example. For example, genomic sequence information is available via the Microbe Genome Sequencing Project, Department of Energy, U.S.A. and from NCBI. Expressed gene sequence information is available at GenBank. Additionally, expressed gene sequences can be derived from gene expression profiling of microbes of interest. Microarrays representing the genome of a variety of microbes as well as custom microarrays for microbes of interest are available from numerous vendors.

The above described method is useful for the analysis of samples in a variety of diagnostic, drug discovery, and research applications. The above described method is useful for the analysis of biological samples. The term "biological sample," as used herein, refers to a sample obtained from an organism or from components (e.g., cells) of an organism. The sample may be of any biological tissue or fluid. In some cases, the sample will be a "clinical sample" which is a sample derived from a patient. Such samples include, but are not limited to, sputum, blood, blood cells (e.g., white blood cells), tissue or fine needle biopsy samples, urine, peritoneal fluid, and pleural fluid, or cells there from. Biological samples may also include sections of tissues such as frozen sections taken for histological purposes. The subject method also finds use in determining the identity of microbes in water, sewage, air samples, food products, including animals, vegetables, seeds, etc., soil samples, plant samples, microbial culture samples, cell culture samples, tissue culture samples, as well as in human medicine, veterinary medicine, agriculture, food science, bioterrorism, and industrial microbiology, etc. The subject method allows identification of hard to culture microbes since culturing the microbes is not necessary. Consequently, the subject method provides for a rapid detection of microbes in a sample with no waiting period for culturing microbes.

Microbes that might be identified using the subject methods, compositions and kits include but are not limited to: a plurality of species of Gram (+) bacteria, plurality of species of Gram (−) bacteria, a plurality of species of bacteria in the family Enterobacteriaceae, a plurality of species of bacteria in the genus *Enterococcus*, a plurality of species of bacteria in the genus *Staphylococcus*, and a plurality of species of bacteria in the genus *Campylobacter, Escherichia coli* (*E. coli*), *E. coli* of various strains such as, K12-MG1655, CFT073, O157:H7 EDL933, O157:H7 VT2-Sakai, etc., *Streptococcus pneumoniae, Pseudomonas aeruginosa, Staphylococcus aureus*, coagulase-negative staphylococci, a plurality of *Candida* species including *C. ablbicans, C. tropicalis, C. dublinlensis, C. viswanathii, C. parapsilosis, Klebsiella pneumoniae*, a plurality of *Mycobacterium* species such as *M. tuberculosis, M. bovis, M. bovis* BCG, *M. scrofulaceum, M. kansasii, M. chelonae, M. gordonae, M. ulcerans, M. genavense, M. xenoi, M. simiae, M. fortuilum, M. malmoense, M. celatum, M. haemophilum* and *M. africanum. Listeria* species, *Chlamydia* species, *Mycoplasma* species, *Salmonella* species, *Brucella* species, *Yersinia* species, etc. Thus, the subject method enables identification of microbes to the level of the genus, species, sub-species, strain or variant of the microbe.

Method of Screening for a Cas9 Variant

Also provided herein is a method of screening for a Cas9 variant that has improved activity (e.g., one that produces more blunt ended breaks).

In certain embodiments, this method comprises:
(a) combining, in a cell, a test Cas9 protein and a Cas9 guide RNA with a target plasmid that comprises a marker that is disrupted by an insert, wherein:
(i) the marker can be reconstituted by blunt end cleavage at sites that flank the insert and re-ligation of the marker sequence, and (ii) the Cas9 guide RNA targets the Cas9 protein to the sites that flank the insert; and (b) determining whether the cell expresses the marker.

In some embodiments, the marker is an antibiotic marker.

In some embodiments, the marker is a colorigenic marker.

In some embodiments, the marker is a light-emitting marker.

In some embodiments, the test Cas9 protein is variant of wild type Cas9 protein that contains up to 20 amino acid substitutions relative to the wild type Cas9 protein.

In some embodiments, the method comprises:

(a) combining, in a population of cells, a library of nucleic acids that encode at least 100 Cas9 variants and a Cas9 guide RNA with a target plasmid that comprises a disrupted marker, wherein (i) the marker is disrupted by an insert, (ii) the marker can be reconstituted by blunt end cleavage at sites that flank the insert and re-ligation of the marker sequence, and (iii) the Cas9 guide RNA targets the Cas9 protein to the sites that flank the insert; and (b) screening the cells for expression of the marker In some embodiments, the method may further comprise sequencing cells expressing the marker, thereby providing the amino acid sequence of an improved Cas9 protein.

Cleavage by the Cas9-gRNA complex comprises several steps: tracRNA loading; DNA binding; specific target selection; cleavage by the RuvC-like domain; cleavage by the HNH domain; and release of the cleaved DNA. Inefficiencies in any of these steps may lead to reduced cleavage by Cas9, and some of the steps, such as tracRNA loading, are specific to Cas9.

Cas9 can be evolved in vivo. First, a suitable host such as E. coli can be transformed with a library of protein expression vectors that each contain a variant of Cas9 as well as a corresponding tracRNA. The Cas9 variants can be made by a directed evolution method, e.g., a method described in Otten et al (Biomolecular Engineering 2005 22: 1-9), Reetz et al (Nature Prot. 2007 2: 891-903), Stemmer (Nature 1994 370: 389-391) and Labrou (Curr. Protein Pept. Sci. 2010 11: 91-100). The method may involve error-prone PCR or DNA shuffling, for example and in particular cases may be adapted from phage display, enzyme engineering or zinc finger technologies. Many molecular techniques may be employed in this method, e.g., random PCR mutagenesis, see, e.g., Rice et al. (1992) Proc. Natl. Acad. Sci. USA 89:5467-5471; or, combinatorial multiple cassette mutagenesis, see, e.g., Crameri et al. (1995) Biotechniques 18:194-196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830,721; 5,824,514; 5,811,238, 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly (e.g., GeneReassembly, see, e.g., U.S. Pat. No. 6,537,776), gene site saturation mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

Ideally the cleavage site of Cas9 (as determined by the tracRNA) will be chosen such that the host genome has few or no copies that would be targeted by the enzyme. However, the cells are also transformed with a modified gene for antibiotic resistance, such as the beta-lactamase gene which confers resistance to ampicillin. This resistance gene may reside on the same expression vector as the Cas9, or on another vector, or in the genome. The modification of the resistance gene comprises an interrupting sequence flanked by Cas9 recognition sites. In the absence of Cas9 activity, the interruption in the resistance gene will preclude production of an active resistance protein. However, in the presence of Cas9 activity, the interrupting sequence can be excised by cleavage of both flanking sites and subsequent ligation of the antibiotic resistance gene. In order for the cells to produce active antibiotic resistance genes, the Cas9 protein must efficiently complete the cleavage steps outlined above, leaving DNA ends that are suitable substrates for DNA ligase. Cas9 variants that leave uneven DNA ends, or variants that do not release the cleaved DNA will not leave DNA ends suitable for ligation. In order to select for more specific cleavage by Cas9, single-base variants of the Cas9 target sequence could be included in the Cas9 and/or antibiotic resistance vector. If the Cas9 variant in that cell induces cleavage of these off-target sequences, expression of the Cas9 protein or antibiotic resistance protein will be reduced.

This description is an outline of the method, and the skilled artisan will understand that the expression host, vectors, or resistance genes could be varied without substantially altering the method. Furthermore, in embodiments it may be preferable to use a different reporter gene such as beta-galactosidase or green fluorescent protein in place of the antibiotic resistance gene. In those cases, a colorimetric or fluorescence assay could be used to assay Cas9 activity in vivo.

This method may in certain embodiments comprise: combining, in a population of cells, a library of nucleic acids that encode Cas9 variants (e.g., at least 2, at least 10, at least 1,000, at least 10,000 or at least 100,000 or more variants) and a Cas9 guide RNA with a target plasmid that comprises a disrupted marker, wherein the marker is disrupted by an insert, wherein the marker can be reconstituted by blunt end cleavage at sites that flank the insert and re-ligation of the marker sequence, and the Cas9 guide RNA targets the Cas9 protein to the sites that flank the insert. After the cells have been made, the cells can be selected for expression of the marker (which would be made by cleavage by Cas9, followed by repair). The Cas9-encoding nucleic acid of the selected cells can then be sequenced, thereby providing the amino acid sequence of an improved Cas9 protein.

What is claimed is:

1. A method for fragmenting a sample containing genomic DNA comprising:

combining a sample containing genomic DNA with a plurality of Cas9-gRNA complexes, wherein the Cas9-gRNA complexes comprise a Cas9 protein and a set of at least 10 Cas9-associated guide RNAs that are complementary to different, pre-defined, sites in one or more genomes, wherein each said different, pre-defined, site in the genome is followed by a protospacer adjacent motif, to produce a reaction mixture;

incubating the reaction mixture to produce at least 5 fragments of genomic DNA, wherein at least some of the fragments are of a length in the range of 1 kb to 200 kb; and subjecting the fragments to target enrichment.

2. The method of claim 1, where the different, pre-defined, sites are chosen so that at least 95% of the fragments have a size that is within 20% of a chosen size.

3. The method of claim 2, where the chosen size is in the range of 1 kb to 10 kb.

4. The method of claim 2, where the chosen size is in the range of 10 kb to 100 kb.

5. The method of claim 1, wherein the enrichment comprises:

hybridizing one or more of the fragments to one or more biotinylated probes, wherein each probe hybridizes to both ends of one of the fragments to form a circular fragment;

retrieving the hybridized fragments with magnetic streptavidin beads;

closing the circular fragments by ligation; and amplifying the circular fragments.

6. The method of claim 1, wherein the enrichment comprises:

hybridizing one or more of the fragments to one or more biotinylated RNA baits;

retrieving the hybridized fragments with magnetic streptavidin beads; and amplifying the fragments.

7. The method of claim 1, wherein one or more of the guide RNAs comprise modified nucleotides.

8. The method of claim 1, wherein the fragments are subjected to gel electrophoresis.

9. The method of claim 1, further comprising ligating an adaptor to one or more of the fragments.

10. The method of claim 9, where the adaptor is a hairpin adaptor.

11. The method of claim 9, where the adaptor is composed of two distinct oligonucleotide molecules that are base paired with one another.

12. The method of claim 1, further comprising sequencing the fragments.

13. The method of claim 12, further comprising sequencing the fragments without amplification.

14. The method of claim 12, wherein the fragments are sequenced using nanopore sequencing.

15. The method of claim 12, wherein the fragments are sequenced using a single molecule sequencing by synthesis method.

16. The method of claim 1, further comprising insertion of sequences in the genomic DNA at or proximal to said different, predefined sites in one or more genomes.

17. The method of claim 1, further comprising amplifying one or more of the fragments.

18. The method of claim 1, wherein the genomic DNA comprises microbial DNA.

19. The method of claim 6, further comprising:

digesting the RNA baits hybridized to the fragments.

20. The method of claim 1, where the enrichment comprises:

hybridizing one or more fragments to one or more biotinylated oligonucleotides;

retrieving the hybridized fragments with magnetic streptavidin beads;

and amplifying the fragments.

* * * * *

UNITED STATES PATENT AND TRADEMARK OFFICE
CERTIFICATE OF CORRECTION

PATENT NO. : 10,577,644 B2
APPLICATION NO. : 15/339510
DATED : March 3, 2020
INVENTOR(S) : Brian Jon Peter et al.

Page 1 of 3

It is certified that error appears in the above-identified patent and that said Letters Patent is hereby corrected as shown below:

On the Title Page

In item (72), in Column 1, in "Inventors", Line 5, after "Garden" insert -- City --.

In the Specification

In Column 1, Line 9, delete "No." and insert -- Nos. --, therefor.

In Column 1, Line 10, delete "61/831,061" and insert -- 61/831,061, --, therefor.

In Column 1, Line 48, delete "10," and insert -- $10^4$, --, therefor.

In Column 2, Line 51, delete "ifa" and insert -- if a --, therefor.

In Column 3, Line 32, delete "-LC-Biotin," and insert -- -LC-LC-Biotin, --, therefor.

In Column 3, Lines 44-49, delete "in another embodiment, an adaptor may itself be composed of two distinct oligonucleotide molecules that are base paired with one another. As would be apparent, a ligatable end of an adaptor may be designed to compatible with overhangs made by cleavage by a restriction enzyme, or it may have blunt ends." and insert the same on Column 3, Line 43 as a continuation of the same paragraph.

In Column 4, Line 53, delete "Cas 9" and insert -- Cas9 --, therefor.

In Column 4, Line 65, delete "Type 11" and insert -- Type II --, therefor.

In Column 5, Line 1, delete "Type 11" and insert -- Type II --, therefor.

In Column 5, Line 8, delete "HNH-domain." and insert -- HNH- domain. --, therefor.

Signed and Sealed this
Ninth Day of June, 2020

Andrei Iancu
*Director of the United States Patent and Trademark Office*

CERTIFICATE OF CORRECTION (continued)
U.S. Pat. No. 10,577,644 B2

In Column 5, Line 14, delete "pyrgenes" and insert -- pyogenes --, therefor.

In Column 5, Line 15, delete "DIOA)" and insert -- D10A) --, therefor.

In Column 5, Line 16, delete "by an by an" and insert -- by an --, therefor.

In Column 8, Line 19, delete "1,000)" and insert -- 1,000 --, therefor.

In Column 8, Line 26, delete "cloning," and insert -- cloning. --, therefor.

In Column 8, Line 43, delete "at" and insert -- al --, therefor.

In Column 9, Line 8, delete "Pat Appln" and insert -- Pat. Appln Pub. --, therefor.

In Column 9, Line 14, delete "may" and insert -- may be --, therefor.

In Column 9, Lines 41-42, delete "application" and insert -- application publication --, therefor.

In Column 10, Lines 20-21, delete "Pat Appln Pub No. 200210058802," and insert -- Pat. Appln Pub. No. 2002/0058802, --, therefor.

In Column 11, Line 4, delete "and or" and insert -- and/or --, therefor.

In Column 13, Line 2, delete "activity" and insert -- activity. --, therefor.

In Column 13, Line 51, delete "applications applications," and insert -- applications, --, therefor.

In Column 14, Line 16, delete "DIOA" and insert -- D10A --, therefor.

In Column 14, Line 20, delete "cas9$^{\Delta HNH/\Delta RuvC}$ transposase" and insert -- cas9$^{\Delta HNH/\Delta RuvC}$::transposase --, therefor.

In Column 14, Line 21, delete "ISY 100)" and insert -- ISY100) --, therefor.

In Column 14, Line 41, delete "029." and insert -- Φ29. --, therefor.

In Column 14, Line 42, delete "029" and insert -- Φ29 --, therefor.

In Column 14, Line 67, delete "'terminal" and insert -- terminal --, therefor.

In Column 15, Line 20, delete "cas9::transposase-029" and insert -- cas9::transposase-Φ29 --, therefor.

In Column 15, Line 47, delete "plasmid:" and insert -- plasmid; --, therefor.

In Column 15, Line 56, delete "host" and insert -- host. --, therefor.

CERTIFICATE OF CORRECTION (continued)
U.S. Pat. No. 10,577,644 B2

In Column 16, Line 17, delete "(ie" and insert -- (i.e. --, therefor.

In Column 16, Line 44, delete "Cinzia)" and insert -- Cinziae) --, therefor.

In Column 17, Line 50, delete "Project," and insert -- Project; --, therefor.

In Column 19, Line 3, delete "S Many" and insert -- Many --, therefor.

In Column 19, Line 14, delete "can" and insert -- that can --, therefor.

In Column 19, Line 59, delete "1 (00,000" and insert -- 100,000 --, therefor.

In Column 20, Line 45, delete "ablbicans," and insert -- albicans, --, therefor.

In Column 20, Line 46, delete "dublinlensis," and insert -- dubliniensis, --, therefor.

In Column 20, Line 50, delete "xenoi," and insert -- xenopi, --, therefor.

In Column 20, Line 50, delete "fortuilum," and insert -- fortuitum, --, therefor.

In Column 20, Lines 51-52, delete "africanum." and insert -- africanum, --, therefor.

In Column 21, Line 21, delete "marker" and insert -- marker. --, therefor.

In Column 21, Line 26, delete "tracRNA" and insert -- tracrRNA --, therefor.

In Column 21, Line 30, delete "tracRNA" and insert -- tracrRNA --, therefor.

In Column 21, Line 35, delete "tracRNA." and insert -- tracrRNA. --, therefor.

In Column 21, Line 52, delete "5,811,238," and insert -- 5,811,238; --, therefor.

In Column 22, Line 5, delete "tracRNA)" and insert -- tracrRNA) --, therefor.